United States Patent [19]

Hanson et al.

[11] Patent Number: 5,508,295
[45] Date of Patent: Apr. 16, 1996

[54] USE OF AMINO ACYL AMINO PROPARGYL DIOL COMPOUNDS FOR TREATMENT OF GLAUCOMA

[75] Inventors: Gunnar J. Hanson, Skokie, Ill.; J. Timothy Keane, Clayton, Mo.

[73] Assignee: G. D. Searle & Co., Chicago, Ill.

[21] Appl. No.: 182,005

[22] PCT Filed: Oct. 22, 1992

[86] PCT No.: PCT/US92/08841

§ 371 Date: Jan. 13, 1994

§ 102(e) Date: Jan. 13, 1994

[87] PCT Pub. No.: WO93/09108

PCT Pub. Date: May 13, 1993

Related U.S. Application Data

[63] Continuation-in-part of Ser. No. 784,276, Oct. 29, 1991, Pat. No. 5,330,996.

[51] Int. Cl.$^6$ ................................................ A61K 31/425
[52] U.S. Cl. ........................................................... 514/365
[58] Field of Search .................................................. 514/305

[56] References Cited

U.S. PATENT DOCUMENTS

| | | | |
|---|---|---|---|
| 4,902,706 | 2/1990 | Hanson et al. | 514/400 |
| 5,032,577 | 7/1991 | Fung et al. | 514/18 |

FOREIGN PATENT DOCUMENTS

| | | | |
|---|---|---|---|
| 128762 | 12/1984 | European Pat. Off. | C07C 103/52 |
| 181110 | 5/1986 | European Pat. Off. | C07K 5/06 |
| 189203 | 7/1986 | European Pat. Off. | C07K 5/00 |
| 186977 | 7/1986 | European Pat. Off. | C07C 103/76 |
| 200406 | 12/1986 | European Pat. Off. | C07D 233/64 |
| 216539 | 4/1987 | European Pat. Off. | C07D 295/18 |
| 229667 | 7/1987 | European Pat. Off. | C07K 5/06 |
| 300189 | 1/1989 | European Pat. Off. | C07D 233/64 |
| 87/04349 | 7/1987 | WIPO | A61K 37/43 |

OTHER PUBLICATIONS

Umezawa et al, in *J. Antibiot.* (Tokyo), 23, 259–262 (1970).
Gross et al, *Science*, 175, 656 (1971).
Boger et al, *Nature*, 303, 81 (1983).
Kokubu et al, *Biochm. Biophys. Res. Commun.*, 118, 929 (1984).
Castro et al, *FEBS Lett.*, 167, 273 (1984).
Hanson et al, *Biochm. Biophys. Res. Comm.*, 132, 155–161 (1985).
Hanson et al, *Biochm. Biophys. Res. Comm.*, 146, 959–963 (1987).

*Primary Examiner*—Robert Gerstl
*Attorney, Agent, or Firm*—J. Timothy Keane

[57] ABSTRACT

Compounds characterized generally as amino acyl amino propargyl diol derivatives are useful in treatment of glaucoma. Compounds of particular interest are those of Formula I

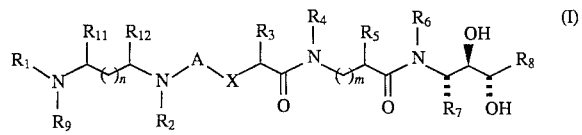

wherein A is selected from CO and $SO_2$; wherein X is selected from oxygen atom and methylene; wherein each of $R_1$ and $R_9$ is a group independently selected from hydrido, methyl, ethyl, n-propyl, isopropyl, benzyl, b,b,b-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, imidazolemethyl, pyridylmethyl and 2-pyridylethyl; wherein $R_5$ is selected from hydrido, alkyl, pyrazolealkyl, pyridylalkyl, thiazolylalkyl, imidazolealkyl, thienylalkyl, furanylalkyl, oxazolylalkyl, isoxazolylalkyl, pyrimidinylalkyl, pyridazinylalkyl and pyrazinylalkyl; wherein each of $R_4$ and $R_6$ is independently selected from hydrido and methyl; wherein $R_7$ is cyclohexylmethyl; wherein $R_8$ is propargyl or a propargyl-containing moiety; wherein each of $R_{11}$ and $R_{12}$ is independently selected from hydrido, alkyl and phenyl; wherein m is zero; and wherein n is a number selected from zero through three; or a pharmaceutically-acceptable salt thereof.

11 Claims, No Drawings

USE OF AMINO ACYL AMINO PROPARGYL DIOL COMPOUNDS FOR TREATMENT OF GLAUCOMA

RELATED APPLICATION

This application is a 371 of PCT/US92/08841 filed Oct. 22, 1992 and a continuation-in-part of U.S. application Ser. No. 07/784,276 filed 29 Oct. 1991 now U.S. Pat. No. 5,330,996.

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23, 259–262 (1970)]. This peptide, known as pepstatin, was found to reduce blood pressure in vivo after the injection of hog renin into nephrectomized rats [Gross et al, *Science*, 175, 656 (1971)]. Pepstatin has the disadvantages of low solubility and of inhibiting acid promeases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim, Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published 18 Dec. 1984, describes dipeptide and tripeptide glyco-containing compounds as renin inhibitors [also see Hanson et al, *Biochm. Biophys. Res Comm.*, 132, 155–161 (1985), 146, 959–963 (1987)]. EP Appl. #181,110, published 14 May 1986, describes dipeptide histidine derivatives as renin inhibitors. EP Appl. #186,977 published 9 Jul. 1986 describes renin-inhibiting compounds containing an alkynyl moiety, specifically a propargyl glycine moiety, attached to the main chain between the N-terminus and the C-terminus, such as N-[4(S)-[(N)-[bis(1 -naphthylmethyl)acetyl]-DL-propargylglycylamino]-3(S)-hydroxy-6-methylheptanoyl]-L-isoleucinol. EP Appl. #189,203, published 30 Jul. 1986, describes peptidyl-aminodiols as renin inhibitors. EP Appl. #200,406, published 10 Dec. 1986, describes alkylnaphthylmethylpropionyl-histidyl aminohydroxy alkanoates as renin inhibitors. EP Appl. #216,539, published 1 Apr. 1987, describes alkylnaphthylmethylpropionyl aminoacyl aminoalkanoate compounds as renin inhibitors orally administered for treatment of renin-associated hypertension. EP Appl. #229,667, published 22 Jul. 1987, describes acyl a-aminoacyl aminodiol compounds having a piperazinylcarbonyl or an alkylaminoalkylcarbonyl terminal group at the N-amino acid terminus, such as 2(S)-{[(1-piperazinyl)carbonyl]-oxy]-3-phenylpropionyl}-Phe-His amide of 2(S)-amino-1-cyclohexyl-3(R), 4(S)-dihydroxy-6-methylheptane. PCT Application No. WO 87/04349, published 30 Jul. 1987, describes aminocarbonyl aminoacyl hydroxyether derivatives having an alkylamino-containing terminal substituent and which are described as having renin-inhibiting activity for use in treating hypertension. EP Appl. #300,189 published 25 Jan. 1989 describes amino acid monohydric derivatives having an alkylamino-alkylamino N-terminus and a b-alanine-histidine or sarcosylhistidine attached to the main chain between the N-terminus and the C-terminus, which derivatives are mentioned as useful in treating hypertension. U.S. Pat. No. 4,902,706 which issued 13 Feb. 1990 describes a series of histidineamide-containing amino alkylaminocarbonyl-H-terminal aminodiol derivatives for use as renin inhibitors U.S. Pat. No. 5,032,577 which issued 16 Jul. 1991 describes a series of histidineamide-aminodiol-containing renin inhibitors.

DESCRIPTION OF THE INVENTION

Amino acyl amino propargyl diol compounds, having utility as renin inhibitors for treatment of hypertension in a subject, constitute a family of compounds of general Formula I:

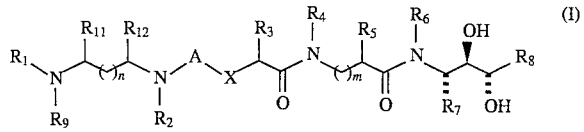

wherein A is selected from methylene, CO, SO and $SO_2$; wherein X is selected from oxygen atom, methylene and

with $R_{10}$ selected from hydrido, alkyl and benzyl; wherein each of $R_1$ and $R_9$ is a group independently selected from hydrido, alkyl, cycloalkyl, alkoxyacyl, haloalkyl, alkoxycarbonyl, benzyloxycarbonyl, loweralkanoyl, haloalkylacyl, phenyl, benzyl, naphthyl, and naphthylmethyl, any one of which groups having a substitutable position may be optionally substituted with one or more radicals selected from alkyl, alkoxy, alkenyl, alkynyl, halo, haloalkyl, cyano and phenyl, and wherein the nitrogen atom to which $R_1$ and $R_9$ are attached may be combined with oxygen to form an N-oxide; wherein $R_2$ is selected from hydrido, alkyl, dialkylaminoalkyl, alkylacylaminoalkyl, benzyl and cycloalkyl; wherein $R_3$ is selected from alkyl, cycloalkylalkyl, acylaminoalkyl, phenylalkyl, naphthylmethyl, aryl; heterocyclicalkyl and heterocycliccycloalkyl wherein the cyclic portion of any of said phenylalkyl, naphthylmethyl, aryl, heterocyclicalkyl and heterocycliccycloalkyl groups may be substituted by one or more radicals selected from halo, hydroxy, alkoxy and alkyl; wherein each of $R_4$ and $R_6$ is independently selected from hydrido, alkyl, benzyl and cycloalkyl; wherein $R_5$ is selected from hydrido, alkyl, benzyl, cycloalkyl, cycloalkylalkyl, alkoxyalkyl, alkylthioalkyl, heteroarylalkyl and heteroarylcycloalkyl; wherein $R_7$ is selected from substituted or unsubstituted alkyl, cycloalkyl, phenyl, cycloalkylalkyl and phenylalkyl, any one of which may be substituted with one or more groups selected from alkyl, hydroxy, alkoxy, halo, haloalkyl, alkenyl, alkynyl and cyano; wherein $R_8$ is selected from

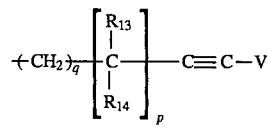

wherein V is selected from hydrido, alkyl, cycloalkyl, haloalkyl, benzyl and phenyl; wherein each of $R_{13}$ and $R_{14}$ is a radical independently selected from hydrido, alkyl, alkenyl, alkynyl, cycloalkyl, phenyl, heterocyclic and heterocyclicalkyl; wherein each of $R_{11}$ and $R_{12}$ is independently selected from hydrido, alkyl, haloalkyl, dialkylamino and phenyl; and wherein m is zero or one; wherein n is a number selected from zero through five; wherein p is a number selected from zero through five; and wherein q is a number selected from zero through five; or a pharmaceutically-acceptable salt thereof.

A preferred family of compounds consists of compounds of Formula I wherein A is selected from methylene, CO, SO and $SO_2$; wherein X is selected from oxygen atom methylene and

with $R_{10}$ selected from hydrido, alkyl and benzyl; wherein each of $R_1$ and $R_9$ is independently selected from hydrido, lower alkyl, haloalkyl, cycloalkyl, alkoxycarbonyl, benzyloxycarbonyl, loweralkanoyl, alkoxyacyl, phenyl and benzyl, and wherein the nitrogen atom to which $R_1$ and $R_9$ are attached may be combined with oxygen to form an N-oxide; wherein each of $R_2$, $R_4$ and $R_6$ is independently selected from hydrido and alkyl; wherein $R_3$ is selected from phenylalkyl, naphthylmethyl, cyclohexylalkyl, cyclopentylalkyl, pyrrolidinyl, piperidinyl, pyrrolidinylmethyl and piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from hydrido, alkyl, benzyl, cycloalkyl, cycloalkylalkyl, alkoxyalkyl, heteroarylalkyl and heteroarylcycloalkyl; wherein $R_7$ is selected from substituted or unsubstituted cyclohexylmethyl and benzyl, either one of which may be substituted with one or more groups selected from alkyl, hydroxy, alkoxy, halo and haloalkyl; wherein $R_8$ is selected from

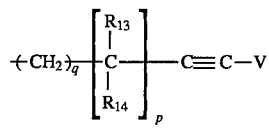

wherein V is selected from hydrido, alkyl, haloalkyl, benzyl and phenyl; wherein each of $R_{13}$ and $R_{14}$ is a radical independently selected from hydrido, alkyl, alkenyl, alkynyl, cycloalkyl, thiazole and thiazolemethyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof.

A more preferred family of compounds consists of compounds of Formula I wherein A is selected from methylene, CO, SO and $SO_2$; wherein X is selected from oxygen atom, methylene and

with $R_{10}$ selected from hyrido, alkyl and benzyl; wherein each of $R_1$ and $R_9$ is independently selected from hydrido, alkyl, alkoxyacyl, haloalkyl, alkoxycarbonyl, benzyloxycarbonyl, and benzyl, and wherein the nitrogen atom to which $R_1$ and $R_9$ are attached may be combined with oxygen to form an N-oxide; wherein each of $R_2$, $R_4$ and $R_6$ is independently selected from hydrido and alkyl; wherein $R_3$ is selected from benzyl, phenethyl, cyclohexylmethyl, phenpropyl, pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from hydrido, alkyl, cycloalkyl, cycloalkylalkyl, alkoxyalkyl, heteroarylalkyl and heteroarylcycloalkyl; wherein $R_7$ is cyclohexylmethyl; wherein $R_8$ is selected from

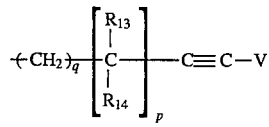

wherein V is selected from hydrido, alkyl and haloalkyl; wherein each of $R_{13}$ and $R_{14}$ is a radical independently selected from hydrido, alkyl, alkenyl and alkynyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof.

An even more preferred family of compounds consists of compounds Formula I wherein A is selected from CO and $SO_2$; wherein x is selected from oxygen atom, methylene and

with $R_{10}$ selected from hydrido and methyl; wherein each of $R_1$ and $R_9$ is independently selected from hydrido, lower alkyl, alkoxyacyl, alkoxycarbonyl, benzyloxycarbonyl, haloalkyl and benzyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, phenethyl, cyclohexylmethyl pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein each of $R_4$ and $R_6$ is independently selected from hydrido and methyl; wherein $R_5$ is selected from hydrido, alkyl, heteroarylalkyl and heteroarylcycloalkyl; wherein $R_7$ is cyclohexylmethyl; wherein $R_8$ is selected from

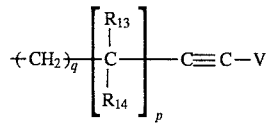

wherein V is selected from hydrido, alkyl and trifluoromethyl; wherein each of $R_{13}$ and $R_{14}$ is a radical independently selected from hydrido, alkyl and alkynyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof.

A highly preferred family of compounds consists of compounds of Formula I wherein A is selected from CO and $SO_2$; wherein X is selected from oxygen atom and methylene; wherein each of $R_1$ and $R_9$ is independently selected from hydrido, methyl, ethyl, n-propyl, isopropyl, benzyl, b,b,b-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, pyrrolidinyl, piperidinyl, pyrrolidinylmethyl, piperidinylmethyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from hydrido, alkyl, pyrazolealkyl, pyridylalkyl, thiazolylalkyl, imidazolealkyl, thienylalkyl, thiazolylcycloalkyl, imidazolecycloalkyl, thienylcycloalkyl, furanylalkyl, oxazolylalkyl, isoxazolylalkyl, pyrimidinylalkyl, pyridazinylalkyl and pyrazinylalkyl; wherein $R_7$ is cyclohexylmethyl; wherein $R_8$ is selected from

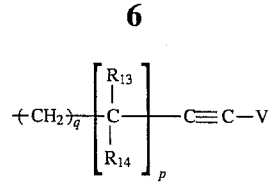

wherein V is selected from hydrido, alkyl and trifluoromethyl; wherein each of $R_{13}$ and $R_{14}$ is a radical independently selected from hydrido, methyl, ethyl, propyl and ethynyl; wherein each of $R_4$ and $R_6$ is independently selected from hydrido and methyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof.

A more highly preferred class of compounds consists of compounds of Formula I wherein A is selected from CO and $SO_2$; wherein X is selected from oxygen atom and methylene; wherein each of $R_1$ and $R_9$ is a group independently selected from hydrido, methyl, ethyl, n-propyl, isopropyl, benzyl, b,b,b-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, imidazolemethyl, pyridylmethyl and 2-pyridylethyl; wherein $R_5$ is selected from hydrido, methyl, ethyl, n-propyl, isopropyl, n-butyl, sec-butyl, iso-butyl, tert-butyl, n-pentyl, isopentyl, neopentyl, n-hexyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, thiazolylcyclopropyl, imidazolecyclopropyl, thienylcyclopropyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_7$ is cyclohexylmethyl; wherein $R_8$ is selected from

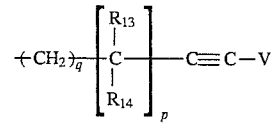

wherein V is selected from hydrido, alkyl and trifluoromethyl; wherein each of $R_{13}$ and $R_{14}$ is a radical independently selected from hydrido, methyl and ethynyl; wherein each of $R_4$ and $R_6$ is independently selected from hydrido and methyl; wherein each of $R_{11}$ and $R_{12}$ is independently selected from hydrido, alkyl and phenyl; wherein m is zero; wherein n is a number selected from zero through three; wherein p is a number selected from one through three; and wherein q is zero or one; or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a $—CH_2—$ group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation.

The term "heterocyclic", as used alone or within groups such as "heterocyclicalkyl", and "heterocycliccycloalkyl", (hereinafter referred to as "heterocyclic-containing groups") embraces radicals having a saturated, or partially unsaturated, or fully saturated heterocyclic group, wherein the cyclic portion consists of a ring system having one ring or two fused rings, which ring system contains one, two or three hetero atoms as ring members selected from nitrogen, oxygen and sulfur, and which ring system has 4 to about 12 ring members. Examples of saturated heterocyclic-containing groups are pyrrolidinyl, piperidinyl, pyrrolidinylmethyl, piperidinylmethyl, pyrrolidinylcyclopropyl and piperidinylcyclopropyl. The term "heteroaryl", whether used alone or within the greater terms "heteroarylalkyl" or "heteroarylcycloalkyl", denotes a subset of "heterocyclic-containing groups" having a cyclic portion which is fully-unsaturated, that is, aromatic in character, and which has one or two hetero atoms as ring members, said hetero atoms selected from oxygen, sulfur and nitrogen atoms, and which ring system has five or six ring members. The "heteroaryl" ring may be attached to a linear or branched alkyl radical having one to about ten carbon atoms or may be attached to a cycloalkyl radical having three to about nine carbon atoms. Examples of such heteroarylalkyl or heteroarylcycloalkyl groups are pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, thiazolylcyclopropyl, imidazolecyclopropyl, thienylcyclopropyl, isoxazolemethyl, isoxazoleethyl, pyridazinemethyl, pyridazineethyl, pyrazinemethyl and pyrazineethyl. The "heterocyclic" portion or "heteroaryl" portion of the radical, as well as the alkyl or cycloalkyl portion of groups containing a "heterocyclic" or "heteroaryl" portion, may be substituted at a substitutable position with one or more groups selected from oxo, alkyl, alkoxy, halo, haloalkyl, cyano, aralkyl, aralkoxy, aryl and aryloxy. Such "heterocyclic", "heterocyclic"-containing group, or "heteroaryl" group may be attached as a substituent through a carbon atom of the hetero ring system, or may be attached through a carbon atom of a moiety substituted on a hetero ring-member carbon atom, for example, through the methylene substituent of an imidazolemethyl moiety. Also, a heterocyclic or heterocyclic-containing group may be attached through a ring nitrogen atom. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in-the family of compounds of Formula I are isomeric forms, including diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, b-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. Also included within the phrase "pharmaceutically-acceptable salts" are "quaternary" salts or salts of "onium" cations, such as ammonium, morpholinium and piperazinium cations, as well as any substituted derivatives of these cations where the salt is formed on the nitrogen atom lone pair of electrons. All of these salts may be prepared by conventional means from the corresponding compound of Formula I by reacting, for example, the appropriate acid or base with the compound of Formula I.

Compounds of Formula I would be useful to treat various circulatory-related disorders. As used herein, the term "circulatory-related" disorder is intended to embrace cardiovascular disorders and disorders of the circulatory system, as well as disorders related to the circulatory system such as ophthalmic disorders including glaucoma. In particular, compounds of Formula I would be useful to inhibit enzymatic conversion of angiotensinogen to angiotensin I. When administered orally, a compound of Formula I would be expected to inhibit plasma renin activity and, consequently, lower blood pressure in a patient such as a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a subject suffering from or afflicted with the effects of hypertension or susceptible to a hypertensive condition if not treated to prevent or control such hypertension. Other examples of circulatory-related disorders which could be treated by compounds of the invention include congestive heart failure, renal failure and glaucoma.

Description of the Synthetic Methods for the Preparation of the Renin Inhibitors of the Invention

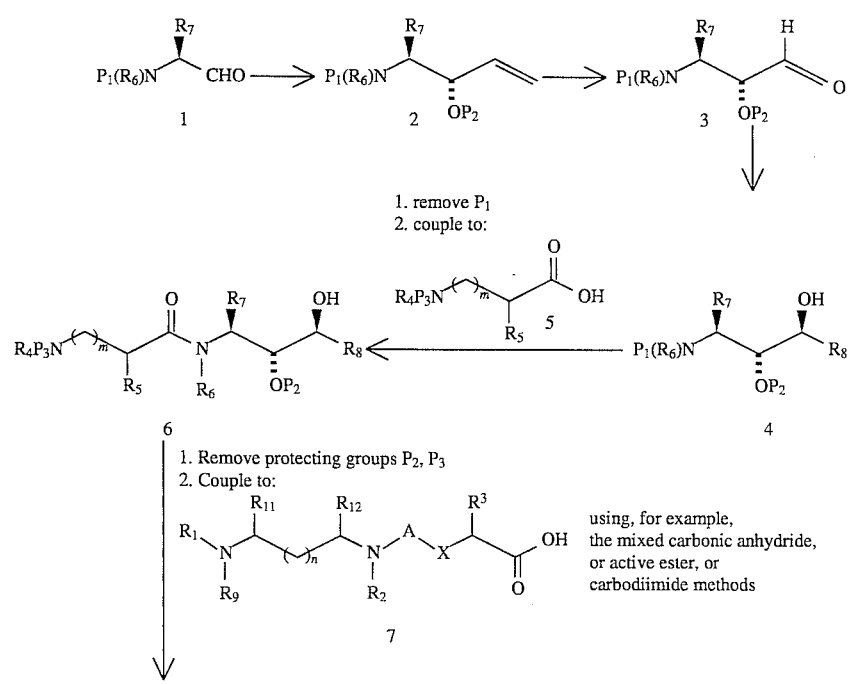

-continued
Synthetic Scheme 1

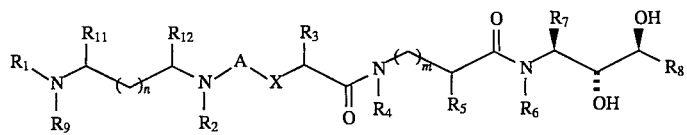

Formula I

Synthetic Scheme 1

(Preparation of Compounds of Formula I)

A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceeding process is exemplified in Hanson, et al., *J. Org. Chem*, 50, 5399 (1985). This aldehyde is reacted with an organometallic reagent such as propargylmagnesium bromide to give intermediate 4. Other suitable organometallic reagents include ethynylmagnesium bromide, 1-methylpropynylmagnesium bromide, 3-methyl-propynyl-magnesium bromide, butynylmagnesium bromide and pentynylmagnesium bromide, but the choices are not limited to these reagents. Compound 4 is deprotected then coupled, using standard amide/peptide coupling methodology, to protected amino acid derivatives 5 (such as Boc-thiazolyl-alanine or Boc-histidine or Boc-pyridylalanine) to give compound 6. These standard coupling procedures such as the carbodiimide, active ester (N-hydroxysuccinimide), and mixed carbonic anhydride methods are shown in Benoiton, et al. J. Org. Chem. 48, 2939 (1983) and Bodansky et al."Peptide Synthesis", Wiley (1976). Intermediate 6 is then deprotected, then coupled to intermediate 7 using the standard amide/peptide coupling methodology, to give compounds of Formula I. Suitable protecting groups may be selected from among those reviewed by R. Geiger in "The Peptides", Academic Press, New York vol. 2 (1979). For example, $P_1$ may by Boc or Cbz; $P_2$ may be a typical oxygen protective group such as acetyl or t-butyldimethylsilyl.

Synthetic Scheme 2

Preparation of 7:

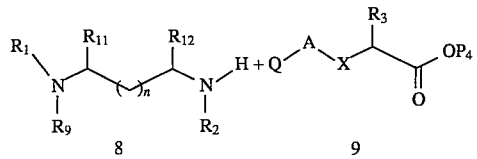

1. remove protecting groups, except $P_4$
2. coupling reaction of 8 + 9
3. remove $P_4$

↓

7

Synthetic Scheme 2

(Preparation of Compounds of Formula I)

Intermediate 7 may be prepared according to the schematic of Synthetic Scheme 2. Intermediate 7 is prepared by coupling amine 8 to mono-protected carboxylic acid 9.

Carboxylic acid 9 is a mono-activated moiety by virtue of a suitable leaving group Q which may be chloride, bromide, fluoride, N-hydroxysuccinimido, p-toluenesulfonyloxy or isobutyloxycarbonyloxy, but is not limited to these groups. After coupling, protecting group $P_4$ is removed (if $P_4$ is a benzyl group, hydrogenolysis over palladium-on-carbon (Pd—C) is performed) to give intermediate amino acid 7.

Synthetic Scheme 3

Preparation of Intermediate 8

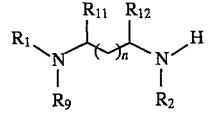

8

Preparation of 8, a non-cyclized diamine:

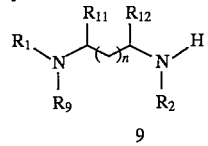

9

Preparation of 8:

8a:

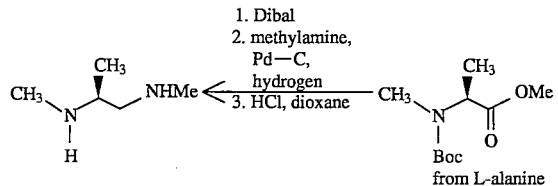

from L-alanine

8b:

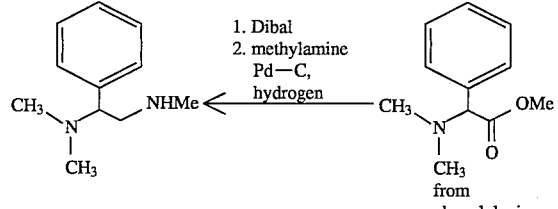

from phenylglycine

8c:

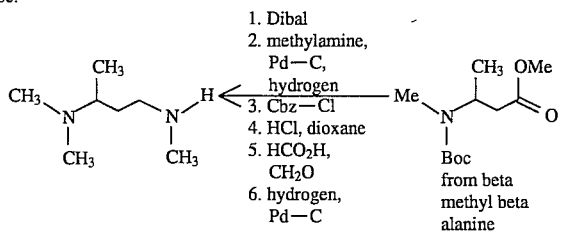

from beta methyl beta alanine

Synthetic Scheme 3

(Preparation of Compounds of Formula I)

Synthetic Scheme 3 describes the preparation of intermediate 8, a non-cyclic diamine. Many of the members of this class, such as ethylene diamine, N,N,N'-trimethylethylene diamine, N,N'-dimethylethylene diamine, N,N'-dimethylpropylene diamine, etc. are commercially available starting materials. Other substituted diamines such as compounds 8a through 8c are obtainable by the procedures depicted in Scheme 3. For example, Boc-L-alanine methyl ester is reduced with diisobutylaluminum hydride to give the corresponding aldehyde which is then reductively aminated with methylamine, then the Boc group is cleaved to give 8a. Alternatively, the procedure of Miller, et al. J. Med. Chem. 19, 1382 (1976) may be employed to give intermediate 8. In another example, a suitably protected diamine is treated with trifluoroacetaldehyde in the presence of sodium cyanoborohydride to give an trifluoroethyl substituent on nitrogen, followed by deprotection to give amine 8.

Abbreviations used:

P1 is an N-protecting group; P2 is H or an oxygen protecting group; P3 is an N-protecting group; P4 is an oxygen protecting group such as benzyl or methyl; Q is a leaving group; Boc is t-butyloxycarbonyl; Cbz is carbobenzoxy.

The following Steps 1–14 constitute specific exemplification of methods to prepare starting materials and intermediates embraced by the foregoing generic synthetic schemes. Those skilled in the art will readily understand that known variations of the conditions and processes of the following preparative procedures can be used to prepare the compounds of Steps 1–14. All temperatures expressed are in degrees Centigrade.

Compounds of Examples 1–24 may be prepared by using the procedures described in the following Steps 1–14:

Step 1

(3S,4S )-N-[(tert-Butyloxy)carbonyl]-4-amino-5-phenyl-3-(triisopromylsilyloxy)pentene:

A solution of (3S,4S)-N-[(tert-butyloxy)carbonyl]-4-amino-3-hydroxy-5-phenyl pentene [prepared by the method of Hanson, et al., J. Org. Chem. 50, 5399 (1985) ] (10.0 g, 64.5 mmol), imidazole (9.14 g, 134 mmol), and chlorotriisopropylsilane (12.44 g, 43.3 mmol) in anhydrous DMF (40 mL) was stirred for 5 days at room temperature under an $N_2$ atmosphere. The solution was poured into $H_2O$ (500 mL) and extracted with $Et_2O$ (2×25 mL). The combined organic layers were washed with $H_2O$ (250 mL), a 0.5M citric acid solution (2×120 mL), a 5% $KHCO_3$ solution (2×100 mL), and brine (2×100 mL). After the organic layer was dried over $MgSO_4$, the filtrate was concentrated and purified by medium pressure column chromatography (silica gel, 10% ethyl acetate in hexane, $R_f$ 0.23) to give 12.9 g (82% yield) of the title compound as a clear, colorless oil. $^1H$ and $^{13}C$ NMR spectral data were consistent with the proposed structure.

Step 2

(2R,3S)-N-[(tert-Butyloxy)carbonyl]-3-amino-4-phenyl-2-(triisopropylsilyloxy)butan-1-ol:

A −78° C. solution of the title compound of Step 1 (12.7 g, 29.3 mmol) in MeOH (81 mL) and $CH_2Cl_2$ (244 mL) was treated with ozone until the solution turned blue. The solution was purged with $O_2$ until the color disappeared and then $NaBH_4$ (3.05 g, 80.5 mmol) was added. After 3 hours at −78° C., the solution was allowed to warm up to room temperature. The reaction solution was poured into $H_2O$ (200 mL) and extracted with ether (3×120 mL). The combined organic layers were washed with brine (2×100 mL) and then dried over $Na_2SO_4$. The filtrate was concentrated to give the title compound as a white solid (13.06 g) $^1H$ and $^{13}C$ NMR spectral data were consistent with the proposed structure.

Step 3

(2R,3S)-N-[(tert-Butyloxy)carbonyl]-3-amino-4-cyclohexyl-2-(triisopropylsilyloxy)butan-1-ol The alcohol of Step 2 (12.8 g, 29.3 mmol) was dissolved in MeOH (135 mL) and hydrogenated with 5% Rh/C at 60 psi and 60° C. for 30 hours. The filtrate was concentrated and purified by medium pressure column chromatography (silica gel, 15% ethyl acetate in hexane) to give the title compound as a white solid (8.70 g, 67% yield, mp 61°–63° C.).

Anal. calcd. for $C_{24}H_{49}NO_4Si$: C, 64.96; H, 11.13; N, 3.16. Found: C, 65.16; H, 11.26; N, 3.12.

Step 4

(2R,3S)-N-[(tert-Butyloxy)carbonyl]-3-amino-4-cyclohexyl-2-(triisopropylsilyloxy)butanal Freshly distilled dimethyl sulfoxide (0.85 g, 10.8 mmol) was added by syringe to a −78° C. solution of oxalyl chloride (0.69 g, 5.41 mmol) in anhydrous THF (22.6 mL). After 10 minutes, the alcohol of Step 3 (2 g, 4.51 mmol) in anhydrous THF (2.3 mL) was added over a period of 1.2 minutes to the −78° C. solution. The solution was stirred for 20 min. and then triethylamine (2.28 g, 22.6 mmol) was added dropwise. The 78° C. bath was removed and the reaction solution was allowed to warm to room temperature. After 1 hour at room temperature, the white, opaque mixture was poured into $H_2O$ (25 mL). The solution was extracted with ether (2×5 mL). The combined organic layers were washed with 1N HCl (25 mL), 5% $NaHCO_3$ (25 mL) and brine (25 mL), and then dried with $MgSO_4$. The filtrate was concentrated at 30° C. in vacuo to give the title compound as a clear, pale yellow liquid (2.08 g, 104% crude yield, TLC, 10% ethyl acetate in hexane, $R_f$ 0.32). $^1H$ and $^{13}C$ NMR spectral data were consistent with the proposed structure.

Step 5

(4S,5R,6S)-N-[(tert-Butyloxy)carbonyl]-6-amino-7-cyclohexyl-4-hydroxy-5 -(triisopropylsilyloxy)hept-1-yne To a dry flask under an $N_2$ atmosphere was added Mg (0.40 g, 6.4 mmol), $HgCl_2$ (0.03 g) and anhydrous diethyl ether (4 mL). A solution of 80% propargyl bromide in toluene (1.83 mL, 16.4 mmol) was added to an addition funnel and several drops were added to the reaction mixture. After the reaction was initiated, anhydrous diethyl ether (10 mL) was added to the reaction flask and anhydrous diethyl ether (10 mL) was added to the funnel solution. The funnel solution was added dropwise while the reaction solution was cooled with a 10° C. bath. The white, opaque mixture was stirred at room temperature for 45 minutes and then a solution of aldehyde of Step 4 (2.05 g, 4.64 mmol) in anhydrous diethyl ether (10 mL) was added dropwise. The yellow, opaque mixture was stirred at room temperature for 2 hours. The mixture was cooled to about 0° C. with an ice-water bath and a saturated $NH_4Cl$ solution (25 mL) was added dropwise. The organic layer was collected and the aqueous layer was extracted with diethyl ether (10 mL). The combined organic layers were washed with $H_2O$ (10 mL) and brine and then dried over $MgSO_4$. The filtrate was concentrated and purified by medium pressure column chromatography (10% EtOH in hexane, silica gel, $R_f$ 0.20) to give the title compound as a clear, pale yellow liquid (1.49 g, 65% yield). The $^1H$ and $^{13}C$ NMR spectral data were consistent with the proposed structure.

Step 6

(4S,5R,6S)-N-[(tert-Butyloxy)carbonyl]-6-amino-7-cyclohexyl-4,5-dihydroxyhept-1-yne:

A solution of the silane of Step 5 in 1.0M tetrabutylammonium fluoride in tetrahydrofuran (21.5 mL, 21.5 mmol) was stirred at room temperature for 60 minutes. The reaction solution was concentrated in vacuo. The concentrate was dissolved in ethyl acetate (160 mL) and was washed with $H_2O$ (3×60 mL) and brine (1×100 mL). After the organic layer was dried with $MgSO_4$, the filtrate was concentrated and purified by medium pressure column chromatography (silica gel, 30% $EtOA_c$ in hexane) to give the title compound as a clear, colorless oil (0.93 g, 53%, $R_f$ 0.16) along with 0.35 g of the epimer (20% yield; $R_f$ 0.04). $^1H$ and $^{13}C$ NMR spectral data for the title compound ($R_f$ 0.16) was consistent with the proposed structure.

Anal. calcd. for $C_{18}H_{31}NO_4$: C, 66.43; H, 9.60; N, 4.30: Found: C, 66.00; H, 9.70; N, 4.20.

Step 7

(4S,5R,6S)-6-amino-7-cyclohexyl-4,5-dihydroxyhept-1-yne

A solution of compound of Step 6 (0.926 g, 2.85 mmol) and trifluoroacetic acid (5.49 mL, 71.3 mmol) in $CH_2Cl_2$ (5.49 mL) was stirred at room temperature for 30 minutes and then concentrated in vacuo. The residue was dissolved in 1.0N KOH (7 mL) and extracted with ethyl acetate (4×10 mL). The combined organic layers were dried over $MgSO_4$ and then concentrated to give the title amine as an off-white solid (0.67 g, 100% yield) $^1H$ and $^{13}C$ NMR spectral data were consistent with the proposed structure.

Step 8

Boc-L-4-thiazolylalanine amide of (4S,5R,6S)-6-amino-7-cyclohexyl-4,5-dihydroxy-1-heptyne Boc-L-3-(4-thiazolyl)alanine (0.24 g, 0.88 mmol), dimethylformamide (2 mL), pyridine (0.07 g) were mixed together and N,N-disuccinimidyl-carbonate (0.227 g, 0.88 mmol) and dimethylaminopyridine (10 mg) were each added in one portion. The mixture was stirred at room temperature for 3 hours. To this solution was then added in one portion the title compound of Step 7 (0.2 g, 0.88 mmol) and the mixture stirred for 12 hours. The solvent was evaporated and the residue taken up on ethyl acetate; this organic solution was washed with 5% potassium carbonate, followed by water, then brine and dried. The solvent was evaporated and the residue chromatographed on silica gel, eluting with 2% ethanol in chloroform to give the title compound (58% yield). The proton NMR was consistent with the proposed structure.

Step 9

L3-(4-thiazolyl)alanine amide of (4S,5R,6S)-6-amino-7-cyclohexyl-4,5-dihydroxy-1-heptyne The title compound of Step 8 (0.25 g, 0.517 mmol) was dissolved in a mixture of trifluoroacetic acid (2 mL) and methylene chloride (2 mL) and stirred for 30 minutes at room temperature. The solvent was then evaporated and the residue treated with 20% sodium hydroxide to bring the pH to 14. The mixture was extracted with ethyl acetate. The organic layer was washed with saturated sodium hydrogen carbonate, water and brine, then dried over magnesium sulfate and evaporated to give the title compound (0.2 g, 0.5 mmol). The proton NMR spectrum was consistent with the proposed structure.

Step 10

2R-(Phenylmethyl)butanedioic acid, 1-(phenylmethyl) ester dicyclohexylammonium salt To a slurry of 4-(4-methoxybenzyl)itaconate (prepared by the method of Talley in U.S. Pat. No. 4,939,288) (50 g) in toluene (250 mL) was added 1,8-diazabicyclo[5.4.0]undec-7-ene (DBU, 30.4 g) in one portion. Then a solution of benzyl bromide (34.2 g) in toluene (50 mL) was added dropwise over 0.5 hour. The reaction was stirred for 0.5 hour at room temperature and then poured into a separatory funnel. The mixture was washed with 3N HCl, aqueous sodium bicarbonate, brine and dried over magnesium sulfate. The solvent was evaporated to give a clear mobile liquid (68 g). Chromatography on silica gel, eluting with from 100% hexane to 25% ethyl acetate gave pure 1-(benzyl)-4-(4-methoxybenzyl) itaconate (55 g, 81% yield). A large Fisher-Porter bottle was charged with this itaconate (41 g), triethylamine (36 g), palladium acetate (380 mg), tri-o-tolylphosphine (1.04 g) and iodobenzene (24.7 g). The bottle was sealed and flushed with nitrogen and placed in an oil bath and heated for 70 minutes. The residue was chromatographed on silica gel, eluting with 100% hexanes until the less polar impurities were removed. Eluting with 10% ethyl acetate in hexane gave the pure phenyl itaconate. This compound (23.8 g) was mixed with toluene (200 mL) and the resulting solution treated with trifluoroacetic acid (30 mL). The solution was stirred at room temperature for 1.5 hour and then evaporated. The residue was taken up in ether (150 mL) and treated with dicyclohexylamine (10.4 g) and stirred at 0° C. whereupon the salt precipitated. This was isolated by filtration and washed with hexane and dried to give pure 1-benzyl 2-benzylidene succinoate dicyclohexylammonium salt (21.24 g, 78% yield). This benzylidene compound (20 g) was place in a Fisher-Porter bottle and also added were degassed methanol (200 mL) and rhodium (R,R)DiPAMP (600 mg) catalyst. The bottle was sealed and flushed with nitrogen then hydrogen. The reaction was hydrogenated at 40 psig for 15 hours at room temperature. The contents were then poured into a round bottom flask (500 mL) and the solvent evaporated to give a dark solid. The residue was taken up in boiling isooctane and allowed to stand, with some title compound crystallizing (7.34 g). The non-dissolved residue was taken up in boiling dimethoxyethane. This solution was allowed to cool for 12 hours, whereupon crystals of the title compound formed (6.05 g). Combining the two crops gave 13.39 g, 66% yield, mp 122°14 125° C. 300 MHz $^1H$ NMR: consistent with proposed structure.

Step 11

2R-(Phenylmethyl)butanedioic acid, 1-(phenylmethyl) ester

The title compound of Step 10 (9.3 g) was suspended in a mixture of water (84 mL) and methanol (8.5 mL). Solid sodium bisulfate (6.12) was added and the mixture stirred for 5 minutes. The mixture was extracted with methylene chloride and the combined extracts were dried over magnesium sulfate and evaporated to dryness. The residue was chromatographed on silica gel, eluting with methanol-chloroform-acetic acid (5:95:0.5), to give the pure title compound (4.3 g, 74% yield).

Step 12

Benzyl aR-[2-[[2-(dimethylamino)ethyl]methylamino]-2-oxoethyl]benzene propanoate The title compound of Step 11 (4.3 g) was dissolved in methylene chloride (20 mL) and N-methyl piperidine (1.86 g) was added. The mixture was cooled to 0° C. and isobutylchloroformate (1.97 g) was added. The mixture was stirred for 10 minutes whereupon N,N,N'-trimethylethylene diamine (2.23 g) in methylene chloride (10 mL) was added. This mixture was stirred at 4° C. for 3 hours, then washed with 1N citric acid, saturated aqueous sodium bicarbonate, water and brine. The solvent was evaporated to give the title compound (4.7 g, 85% yield). 300 MHz $^1$H NMR: consistent with proposed structure.

Step 13 aR-[2-[[2-(dimethylamino)ethyl]methylamino]-2-oxoethyl] benzene propanoic acid

The title compound of Step 12 (4.6 g) was dissolved in ethanol (50 mL) and hydrogenated over 4% Pd—C at 5 psi at room temperature for 17 hours. The ethanol was evaporated to give the title compound (3 g, 71% yield). 300 MHz $^1$H NMR: consistent with proposed structure.

Step 14

O-(N-(dimethylaminoethyl)-N-methyl-aminocarbonyl)-3-L-phenyllactic acid

Benzyl L-3-phenyllactate (14.28 g) was dissolved in tetrahydrofuran (357 mL) and to this was added carbonyl diimidazole (9.78 g) and the mixture was stirred at room temperature for 4 hours. N,N,N'-trimethylethylene diamine (6.8 g) was added and the mixture stirred for 8 hours. The solvent was evaporated and the residue taken up in ether and washed with water, dried over magnesium sulfate and evaporated to give a yellow oil (13 g, 61% yield); 300 MHz $^1$H NMR consistent with proposed structure. This ester was hydrogenated over 4% Pd—C @ 5 psi and room temperature for 3.5 hours in tetrahydrofuran. The title compound was obtained as a white solid (10 g) and recrystallized from methanol.

Anal. calcd for $C_{15}H_{22}N_2O_4+H_2O$: C, 57.68; H, 7.75; N, 8.98. Found: C, 57.60; H, 7.82; N, 8.94.

The following working Examples are provided to illustrate synthesis of Compounds 1–24 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

Example 1

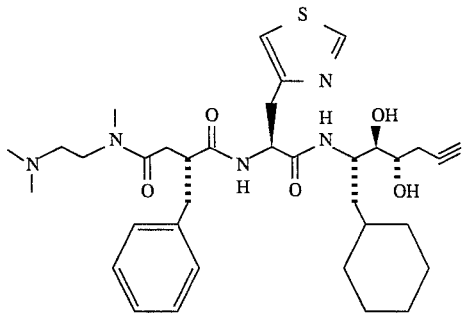

$N^1$-[2-[[1S,1R*-(cyclohexylmethyl-2S*,3R*-dihydroxy-5-hexynyl]amino]-2-oxo-1R*-(4-thiazolylmethyl)ethyl] -$N^4$-[2-(dimethylamino)ethyl]-$N^4$-methyl-2S*-(phenylmethyl)butanediamide The title compound of Step 13 (0.14 g) was dissolved at room temperature in dimethylformamide (1.5 mL) and to this was added N,N'-disuccinimidyl-carbonate (122 mg), pyridine (40 mg) and dimethylaminopyridine (12 mg in 0.5 mL dimethylformamide). The mixture was stirred for 2 hours, whereupon the title amine of Step 9 (174 mg) as a dimethylformamide solution (0.5 mL) was added. This mixture was allowed to stir for 12 hours. The solvent was evaporated and the residue dissolved in ethyl acetate. This mixture is washed successively with 5% potassium carbonate, water and brine, then dried over sodium sulfate and the solvent evaporated to a yellow oil. The residue was purified by chromatography on silica gel, eluting with methylene chloride-methanol-ammonium hydroxide (90:10:1) to afford the pure title compound (170 mg, 56% yield).

Example 2

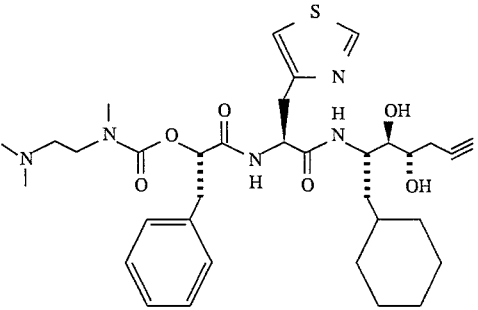

[[[2-[[1S,1R*-(cyclohexylmethyl)-2S*,3R*-dihydroxy-5-hexynyl]amino]-2-oxo-1 R*-(4-thiazolylmethyl)ethyl] amino]-2-oxo-1R*-(phenylmethyl)ethyl][2-(dimethylamino)ethyl]methylcarbamate The title acid of Step 14 is coupled to the title amine of Step 9 using the procedure described for the preparation of Example 1. The crude product is purified by flash chromatography on silica gel, eluting with chloroform-ethanol-ammonium hydroxide (84:15:1), to give title compound.

Compounds #3–24, as shown in Table I below, may be synthesized by reference to the foregoing specific and general procedures for preparing compounds of Formula I.

TABLE I

| Example Compound No. | Structure |
|---|---|
| 3 | 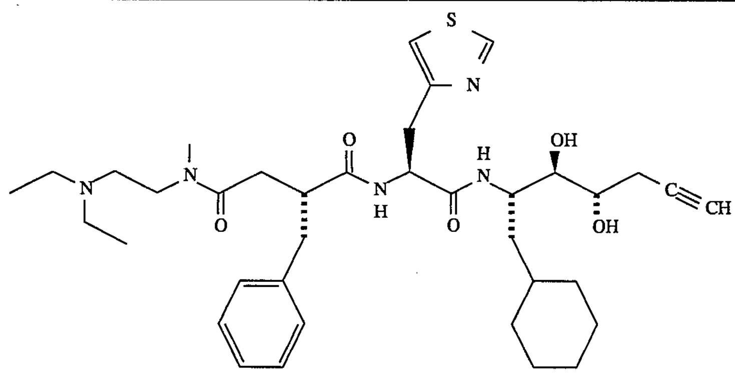 |
| 4 | 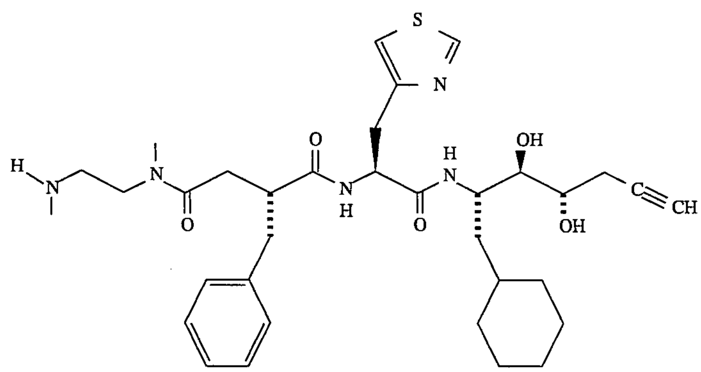 |
| 5 | 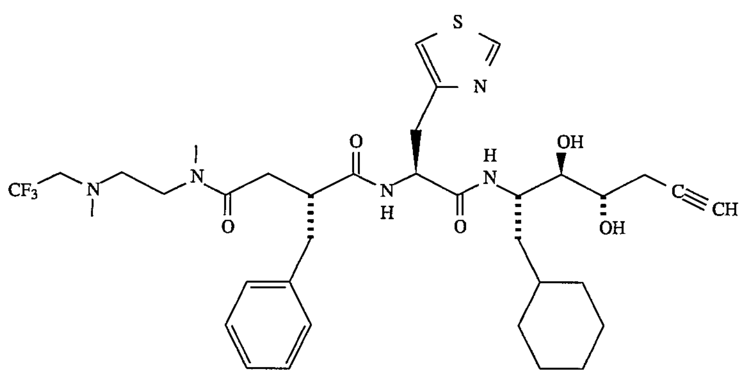 |
| 6 | 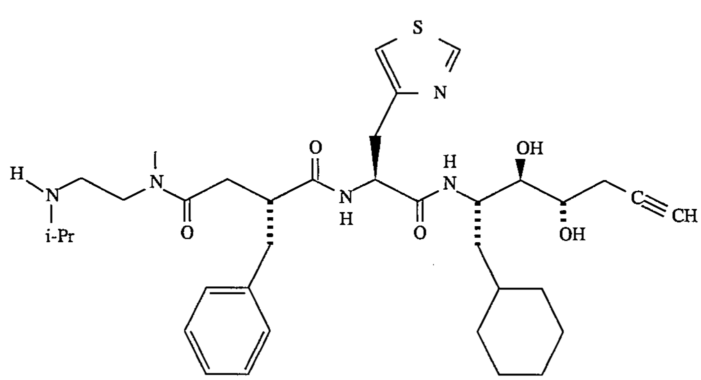 |

TABLE I-continued

| Example Compound No. | Structure |
|---|---|
| 7 | 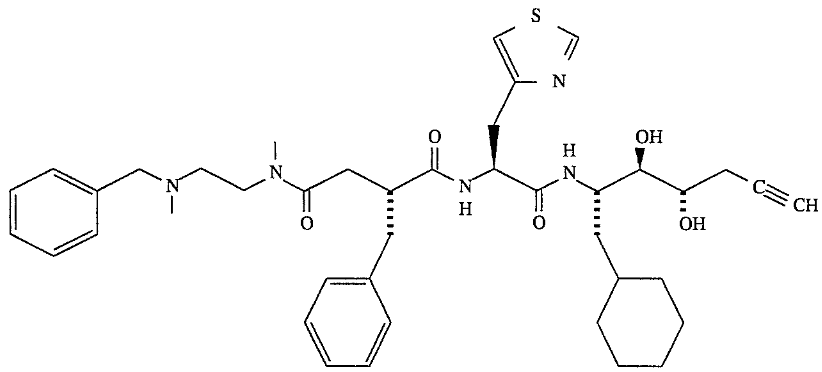 |
| 8 | 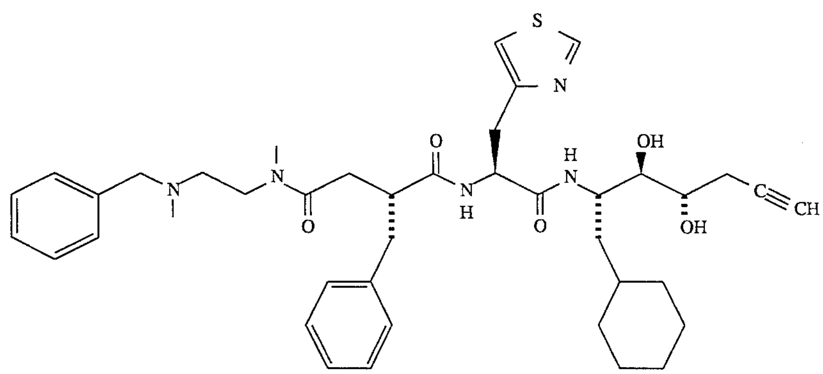 |
| 9 | 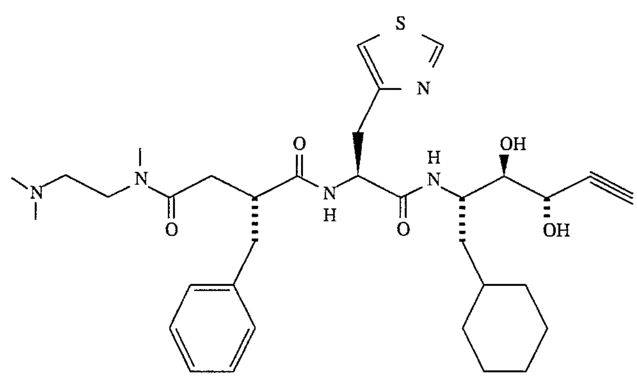 |
| 10 | 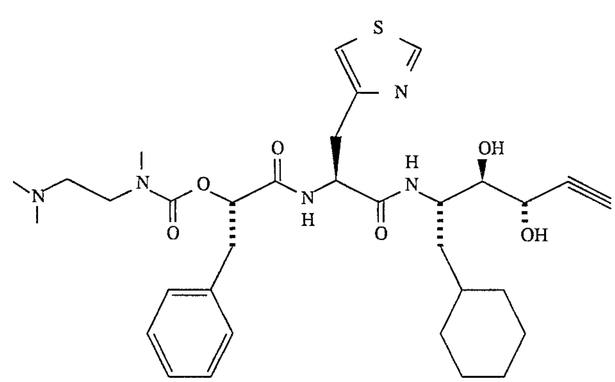 |

TABLE I-continued

| Example Compound No. | Structure |
| --- | --- |
| 11 | 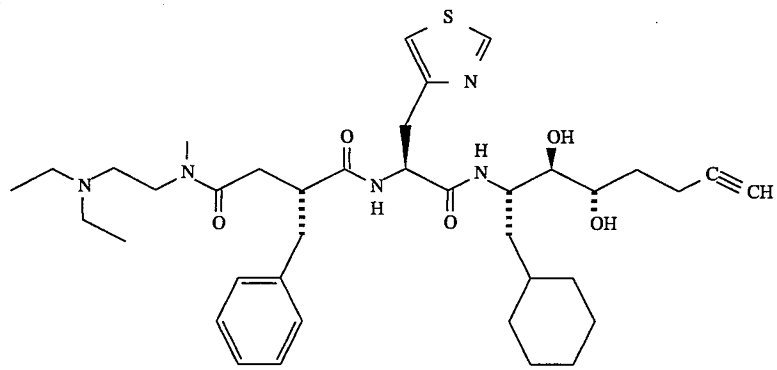 |
| 12 | 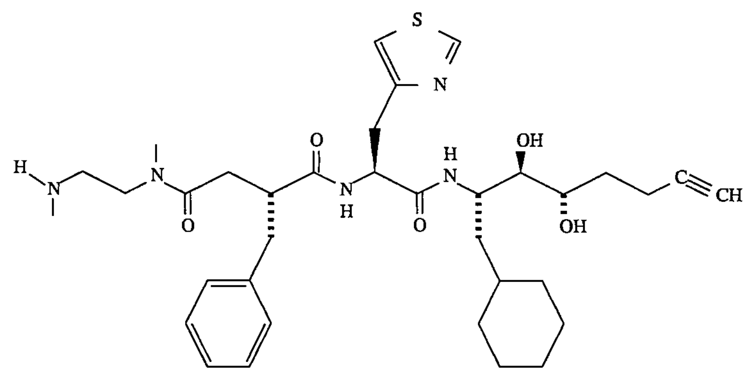 |
| 13 | 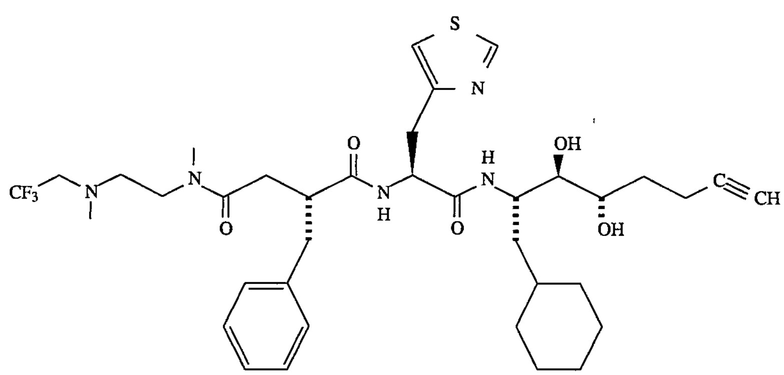 |
| 14 | 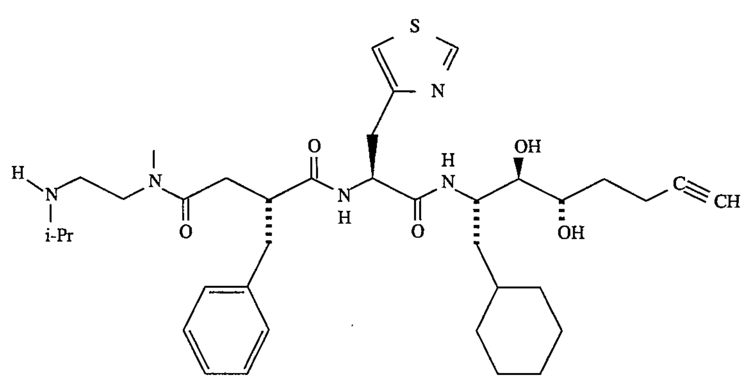 |

TABLE I-continued

| Example Compound No. | Structure |
| --- | --- |
| 15 | 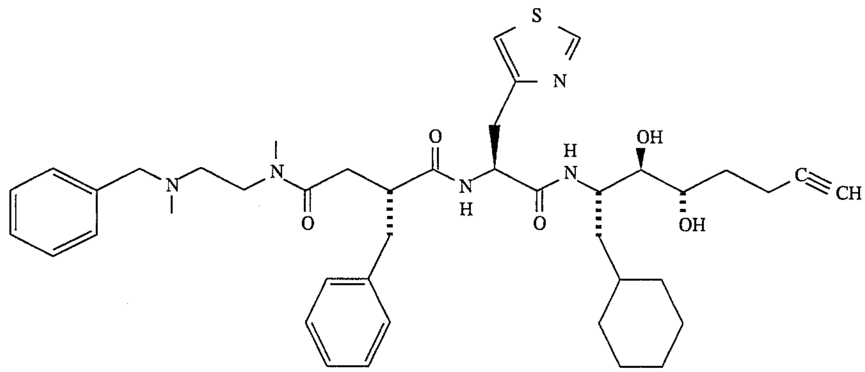 |
| 16 | 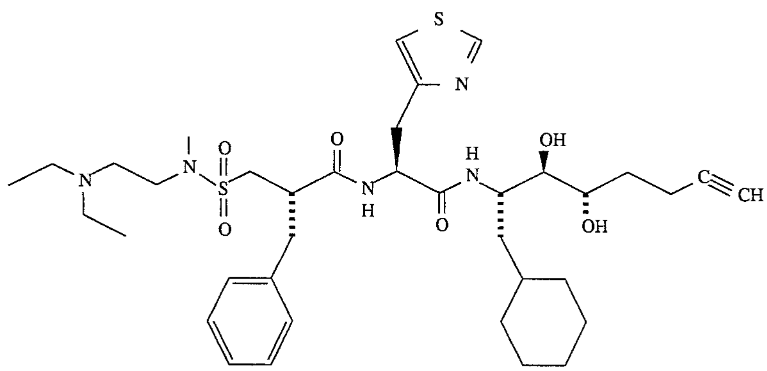 |
| 17 | 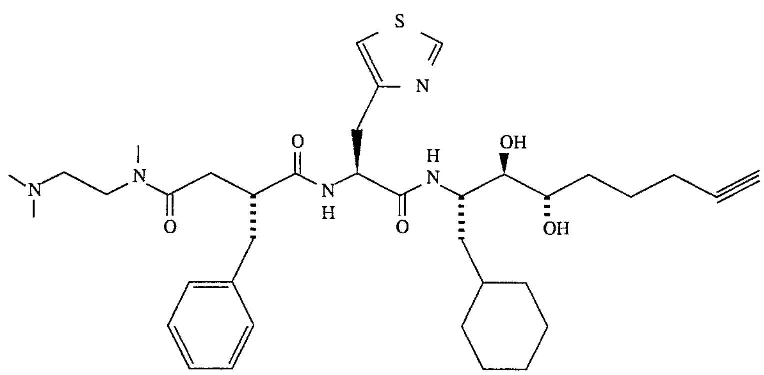 |
| 18 | 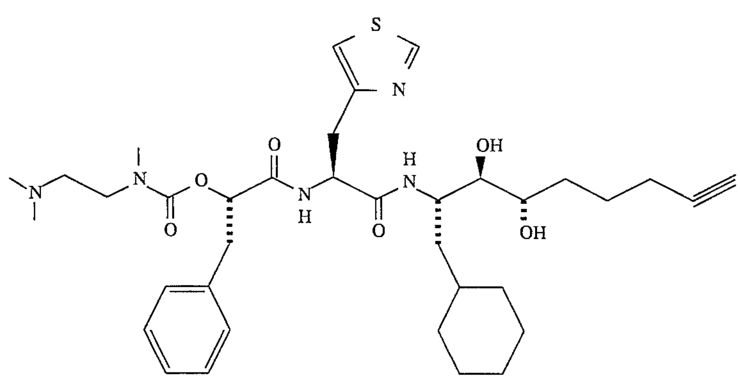 |

TABLE I-continued

| Example Compound No. | Structure |
| --- | --- |
| 19 | 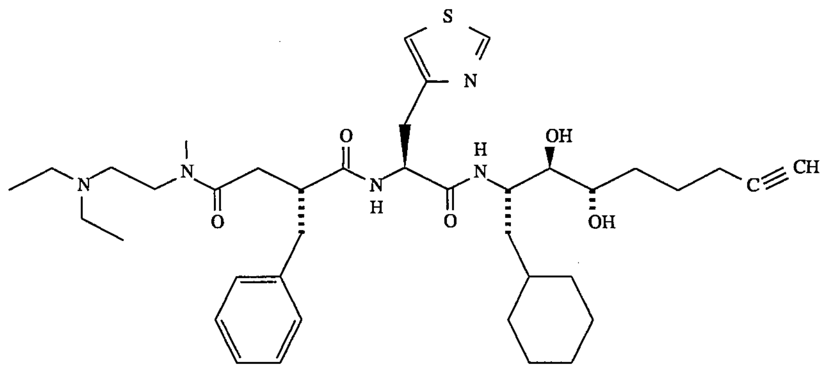 |
| 20 | 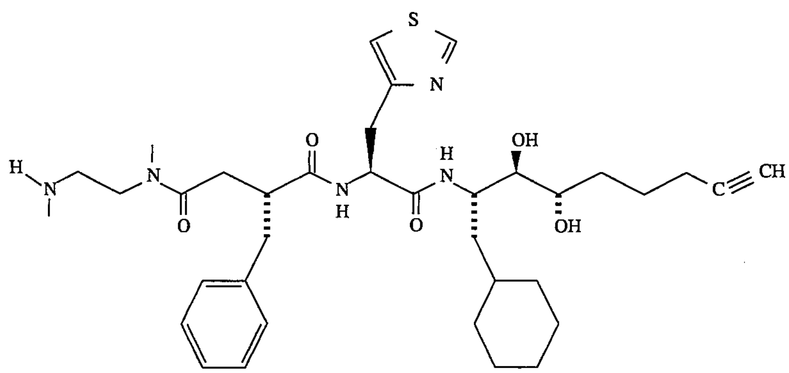 |
| 21 | 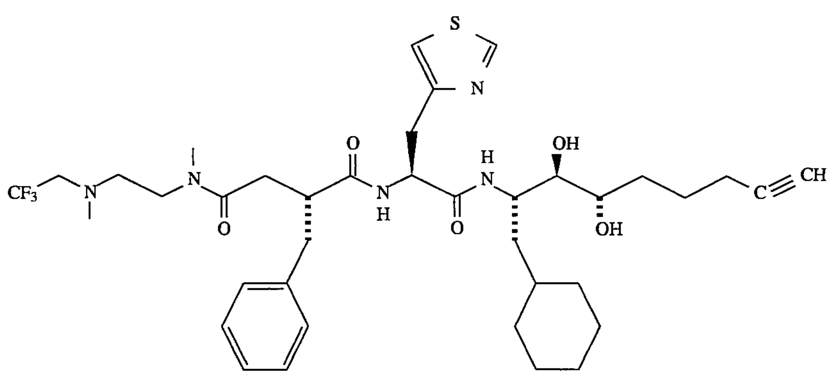 |
| 22 | 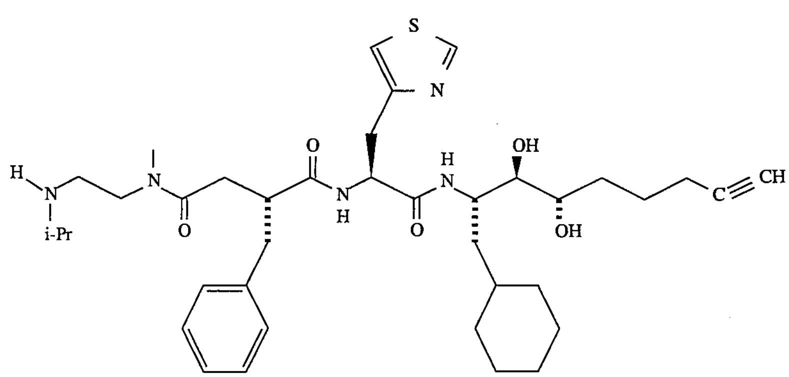 |

TABLE I-continued

| Example Compound No. | Structure |
|---|---|
| 23 | 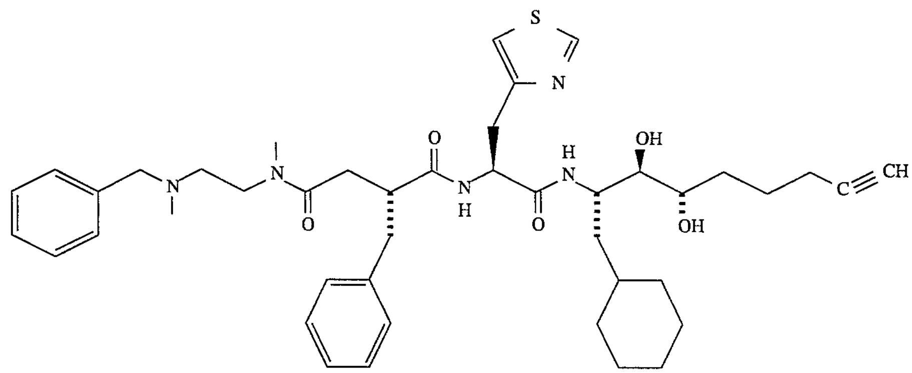 |
| 24 | 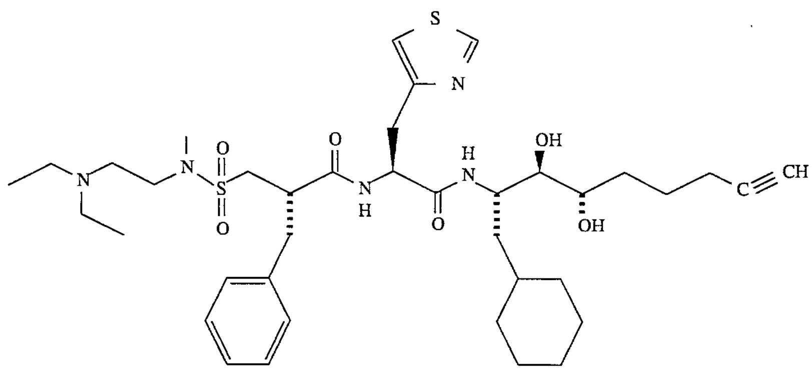 |

BIOLOGICAL EVALUATION

Human Renin Inhibition in vitro

Compounds of Formula I were evaluated as inhibitors of human renin in an in vitro assay, as follows: This human renin inhibition test has been previously described in detail [Papaioannou et al., *Clinical and Experimental Hypertension*, A7(9), 1243–1257 (1985)]. Human renin was obtained from the National Institute for Biological Standards, London. An incubation mixture was prepared containing the following components: in a total volume of 0.25 mL: 100 mM Tris-acetate buffer at pH 7.4, 25×10–6 Goldblatt units of renin, 0.05 mL of plasma from human volunteers taking oral contraceptives, 6.0 mM Na-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity.

The in vitro enzymatic conversion of angiotensinogen to angiotensin I was inhibited by test compounds of the invention as indicated in Table II, below:

TABLE II

| | Human Renin in vitro Inhibition Data |
|---|---|
| Compound Example # | IC50 Human Renin (nM) |
| Example 1 | 28 |

Marmoset Plasma Renin Activity (PRA) Inhibition on Oral Administration

The oral activity of renin inhibitor compounds is determined in vivo in Marmoset monkeys using the following procedure. Common Marmoset monkeys (*Callithrix jacchus*, Charles River, both sexes, body weight 300–400 g) are placed on a modified high-protein low-sodium diet (Purina, St. Louis, Mo.) for 1 week. About 24 hours prior to the administration of test compound, Lasix (5 mg/kg, im) is given. On the day of the test, the animal is anesthetized with isoflurane, body weight recorded, and a baseline blood sample taken. Then, test compound is given intragastrically and blood samples are taken in K-EDTA for plasma renin activity at appropriate time intervals. The PRA is determined by using the protocol outlined below. Results may be expressed in terms of PRA at various time intervals both before and after compound administrations. It is expected that a compound of the invention, when administered orally, would inhibit marmoset plasma renin activity to a level of at about 70% at a dose of 20 mg/kg of body weight.

PLASMA RENIN ACTIVITY ASSAY

I. Angiotensin I Generation

| Plasma Sample | 200 ul |
|---|---|
| PMSF 5% | 1 ul |
| Neomycin 10% | 3 ul |
| 8-HQ 0.5M | 3 ul |
| TES 0.5M, pH 7.4 | 20 ul |

25 ml of the above reaction mixtures, in duplicate, are incubated at 37° C. or 0° C. for 2 hours.

II. Determination of Angiotensin I Concentrations

Angiotensin I (AI) concentrations are determined by radioimmunoassays with a commercial kit from NEN Co.

III. Calculation of Plasma Renin Activity

PRA (ng AI/ml/hr)=(AI at 37°-AI at 0°)/2 hr.
Abbreviations used:
PMSF: Phenylmethylsulfonylfluoride
8-HQ: 8-Hydroxyquinoline
BSA : Bovine Serum Albumin
TES : N-tris[Hydroxymethyl]methyl-2-aminoethane Sulfonic Acid
EDTA: Ethylenediamine Tetraacetic Acid

Determination of Oral Bioavailability

The bioavailability in marmosets and dogs is determined by sampling the blood via the femoral vein at various time points after administering the renin inhibitor compounds of the invention in polyethylene glycol 400 at an intragastric dose of 10 mg/kg or at an intravenous dose of 1 mg/kg. Compound concentration in plasma is determined using the bioassay technique described below. The percent bioavailability is calculated by dividing the area under the concentration-vs.-time curve obtained from the intragastric experiment by the area under the concentration-vs.-time curve obtained from the intravenous experiment (adjusting for different doses), and multiplying the result by 100%. A compound of the invention would be expected to be orally bioavailable in marmoset and dog.

Renin inhibitor plasma concentrations are determined by a bioassay. The plasma samples are extracted with acetonitrile and the extract is evaporated to dryness under nitrogen. Residue is dissolved in 4% bovine serum albumin containing 0.9% NaCl and 5% EDTA. The dissolved residue (0.1 ml) is incubated with a reaction mixture containing human plasma (0.12 ml), 5% phenylmethylsulfonylfluoride (1.2 ul), 10% neomycin (2.4 ul), 0.5M TES buffer (pH 7.4, 24 ul), and 0.6 mU/ml recombinant human renin (1000 U/mg, 50ul) at 37° C. for 90 minutes. The renin activity is determined by a standard angiotensin I radioimmunoassay (New England Nuclear Corp.). The amount of test compound in the plasma is determined by comparing the extent of inhibition of renin activity with that produced by a known amount of test compound added to plasma and analyzed above.

Renin Inhibitor Species Specificity Method

Blood was collected in a 10 ml Becton Dickinson vacutainer tube with 0.1 ml of 15% EDTA (K3) solution (15 mg) from normal animals or high renin animals; i.e., those pre-treated with 5 mg/kg of Lasix® intramuscularly 2 times within a 6 hour interval 24 hours prior to bleeding. The blood was then centrifuged at 2500 RPM for 20 minutes and the plasma from the various species respectively pooled, aliquoted and stored in the freezer. The human plasma source was a male Caucasian taking a prescription of an angiotensin converting enzyme inhibitor.

The plasma renin activity assay is a modification of the human renin inhibition test in that the animal plasma is the source of both the renin substrate and the renin enzyme. In a total volume of 0.1 ml, 90 mM Tris-acetate buffer, pH 7.5, 12 mM sodium EDTA, 0.012 mg/ml neomycin sulfate, 0.9 mg/ml bovine serum albumin, 1.61 mM phenylmethyl sulfonyl fluoride, 4 mM 8-hydroxyquinoline and 0.09 ml of the animal or human plasmas were incubated for 2 hours at 37° C. in a shaking water bath or at 4° C. in an ice bath in the presence or absence of renin inhibitors. The produced angiotensin I was determined by radioimmunoassay (New England Nuclear kit).

The amount of angiotensin I generated during the 2 hours at 4° C. was usually less than 5% of that activity produced at 37° C.; however, the 4° C. background values were nevertheless subtracted from the 37° C. ones for the 100% activity values. The renin inhibitors are assayed in duplicate using 5 concentrations and the data is expressed as a percent of the 100% total renin activity.

The Effect of Compound of the Invention on Marmoset Blood Pressure Reduction on Intravenous Administration The blood pressure reducing activity of the renin inhibitor compound of the invention is determined in vivo in Marmoset monkeys using the following procedure. Common Marmoset monkeys (*Callithrix jacchus*, Charles River, both sexes, body weight ca. 400 g) were placed on a modified high protein low sodium diet (Purina, St. Louis, Mo.) for 1 week. 24 hours prior to the administration of test compound, Lasix (5 mg/kg, im) was given. On the day of the test, the animal was anesthetized with isoflurane, body weight recorded, and the left femoral artery and vein were catheterized. The animal is allowed to regain consciousness and the title compound of Example 1 (100 micrograms/kg) is administered intravenously in 0.1 mL/kg polyethylene glycol 400 at time zero. Mean arterial blood pressure (MABP) in mmHg is then recorded every ten minutes until 120 minutes. It is expected that a compound of the invention would lower blood pressure in salt-depleted, conscious marmosets.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating glaucoma in a subject, said method comprising administering to said subject a therapeutically-effective amount of a compound of Formula I:

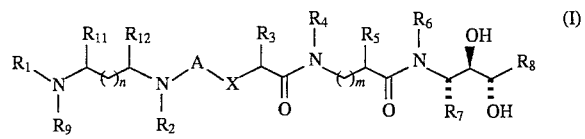

wherein A is selected from methylene, CO, SO and $SO_2$; wherein X is selected from oxygen atom, methylene and

with $R_{10}$ selected from hydrido, alkyl and benzyl; wherein each of $R_1$ and $R_9$ is a group independently selected from hydrido, alkyl, cycloalkyl, alkoxyacyl, haloalkyl, alkoxycarbonyl, benzyloxycarbonyl, loweralkanoyl, haloalkylacyl, phenyl, benzyl, naphthyl, and naphthylmethyl, any one of which groups having a substitutable position may be optionally substituted with one or more radicals selected from alkyl, alkoxy, alkenyl, alkynyl, halo, haloalkyl, cyano and phenyl, and wherein the nitrogen atom to which $R_1$ and $R_9$ are attached may be combined with oxygen to form an N-oxide; wherein $R_2$ is selected from hydrido, alkyl, dialkylaminoalkyl, alkylacylaminoalkyl, benzyl and cycloalkyl; wherein $R_3$ is selected from alkyl, cycloalkylalkyl, acylaminoalkyl, phenylalkyl, naphthylmethyl, aryl, heterocyclicalkyl, heterocycliccycloalkyl, heteroaryl and heteroarylalkyl, wherein the cyclic portion of any of said phenylalkyl, naphthylmethyl, aryl, heterocyclicalkyl, heterocycliccycloalkyl, heteroaryl and heteroarylalkyl groups may be substituted by one or more radicals selected from halo, hydroxy, alkoxy and alkyl; wherein each of $R_4$ and $R_6$ is independently selected from hydrido, alkyl, benzyl and cycloalkyl; wherein $R_5$ is selected from hydrido, alkyl, benzyl, cycloalkyl, cycloalkylalkyl, alkoxyalkyl, alkylthioalkyl, heteroarylalkyl and heteroarylcycloalkyl; wherein $R_7$ is selected from substituted or unsubstituted alkyl, cycloalkyl, phenyl, cycloalkylalkyl and phenylalkyl, any one of which may be substituted with one or more groups selected from alkyl, hydroxy, alkoxy, halo, haloalkyl, alkenyl, alkynyl and cyano; wherein $R_8$ is selected from

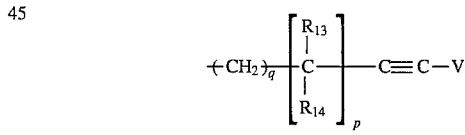

wherein V is selected from hydrido, alkyl, cycloalkyl, haloalkyl, benzyl and phenyl; wherein each of $R_{13}$ and $R_{14}$ is a radical independently selected from hydrido, alkyl, alkenyl, alkynyl, cycloalkyl, phenyl, heterocyclic and heterocyclicalkyl; wherein each of $R_{11}$ and $R_{12}$ is independently selected from hydrido, alkyl, haloalkyl, dialkylamino and phenyl; and wherein m is zero or one; wherein n is a number selected from zero through five; wherein p is a number selected from zero through five; and wherein q is a number selected from zero through five; or a pharmaceutically-acceptable salt thereof;

with the proviso that for any of the foregoing $R^1$ through $R^{14}$ substituents containing a radical selected from alkyl, cycloalkyl, alkenyl, alkynyl, aryl and heterocyclic, the following shall apply:

alkyl is a linear or branched radical having one to about twenty carbon atoms:

cycloalkyl is a cyclic radical having three to about ten carbon-ring atoms:

alkenyl is a linear or branched radical having two to about twenty carbon atoms and containing at least one carbon carbon double bond;

alkynyl is a linear or branched radical having two to about twenty carbon atoms and containing at least one carbon carbon triple bond;

aryl is selected from phenyl, naphthyl and biphenyl;

heterocyclic is a saturated or partially unsaturated radical consisting of a carbocyclic ring system having one ring or two fused rings, which ring system contains one, two or three hetero atoms as ring members selected from nitrogen, oxygen and sulfur atoms, and which ring system has four to about twelve ring members; and heteroaryl is a fully unsaturated radical having a carbocyclic ring system consisting of one ring or two fused rings, said ring selected from five-membered rings containing one, two or three hetero atoms as ring members selected from nitrogen, oxygen, and sulfur atoms.

2. The method of claim 1 wherein A is selected from methylene, CO, SO and $SO_2$; wherein X is selected from oxygen atoms methylene and

with $R_{10}$ selected from hydrido, alkyl and benzyl; wherein each of $R_1$ and $R_9$ is independently selected from hydrido, lower alkyl, haloalkyl, cycloalkyl, alkoxycarbonyl, benzyloxycarbonyl, loweralkanoyl, alkoxyacyl, phenyl and benzyl, and wherein the nitrogen atom to which $R_1$ and $R_9$ are attached may be combined with oxygen to form an N-oxide; wherein each of $R_2$, $R_4$ and $R_6$ is independently selected from hydrido and alkyl; wherein $R_3$ is selected from phenylalkyl, naphthylmethyl, cyclohexylalkyl, cyclopentylalkyl, pyrrolidinyl, piperidinyl, pyrrolidinylmethyl, piperidinylmethyl, pyrazolemethyl, pyrozoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from hydrido, alkyl, benzyl, cycloalkyl, cycloalkylalkyl, alkoxyalkyl, heteroarylalkyl and heteroarylcycloalkyl; wherein $R_7$ is selected from substituted or unsubstituted cyclohexylmethyl and benzyl, either one of which may be substituted with one or more groups selected from alkyl, hydroxy, alkoxy, halo and haloalkyl; wherein $R_8$ is selected from

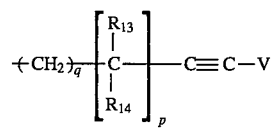

wherein V is selected from hydrido, alkyl, haloalkyl, benzyl and phenyl; wherein each of $R_{13}$ and $R_{14}$ is a radical independently selected from hydrido, alkyl, alkenyl, alkynyl, cycloalkyl, thiazole and thiazolemethyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof;

with the proviso that for any of the foregoing $R^1$ through $R^{14}$ substituents containing a radical selected from alkyl, cycloalkyl, alkenyl, alkynyl, aryl and heterocyclic, the following shall apply:

alkyl is a linear or branched radical having one to about twenty carbon atoms:

cycloalkyl is a cyclic radical having three to about ten carbon-ring atoms:

alkenyl is a linear or branched radical having two to about twenty carbon atoms and containing at least one carbon carbon double bond;

alkynyl is a linear or branched radical having two to about twenty carbon atoms and containing at least one carbon carbon triple bond;

aryl is selected from phenyl, naphthyl and biphenyl; and heteroaryl is a fully unsaturated radical having a carbocyclic ring system consisting of one ring or two fused rings, said ring selected from five-membered rings containing one, two or three hetero atoms as ring members selected from nitrogen, oxygen, and sulfur atoms.

3. The method of claim 2 wherein A is selected from methylene, CO, SO and $SO_2$; wherein X is selected from oxygen atom, methylene and

with $R_{10}$ selected from hydrido, alkyl and benzyl; wherein each of $R_1$ and $R_9$ is independently selected from hydrido, alkyl, alkoxyacyl, haloalkyl, alkoxycarbonyl, benzyloxycarbonyl and benzyl, and wherein the nitrogen atom to which $R_1$ and $R_9$ are attached may be combined with oxygen to form an N-oxide; wherein each of $R_2$, $R_4$ and $R_6$ is independently selected from hydrido and alkyl; wherein $R_3$ is selected from benzyl, phenethyl, cyclohexylmethyl, phenpropyl, pyrrolidinyl, piperidinyl, pyrrolidinylmethyl, piperidinylmethyl, pyrazolemethyl, pyrozoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from hydrido, alkyl, cycloalkyl, cycloalkylalkyl, alkoxyalkyl, heteroarylalkyl and heteroarylcycloalkyl; wherein $R_7$ is cyclohexylmethyl; wherein $R_8$ is selected from

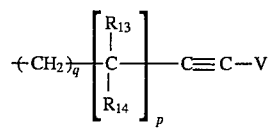

wherein V is selected from hydrido, alkyl and haloalkyl; wherein each of $R_{13}$ and $R_{14}$ is a radical independently selected from hydrido, alkyl, alkenyl and alkynyl; wherein each of $R_{11}$ and $R_{12}$ is independently selected from hydrido, alkyl, dialkylamino and phenyl; wherein m is zero or one; wherein n is a number selected from zero through five; wherein p is a number selected from zero through five; and wherein q is a number selected from zero through five; or a pharmaceutically-acceptable salt thereof;

with the proviso that for any of the foregoing $R^1$ through $R^{14}$ substituents containing a radical selected from alkyl, cycloalkyl, alkenyl, alkynyl, aryl and heterocyclic, the following shall apply:

alkyl is a linear or branched radical having one to about twenty carbon atoms:

cycloalkyl is a cyclic radical having three to about ten carbon-ring atoms:

alkenyl is a linear or branched radical having two to about twenty carbon atoms and containing at least one carbon carbon double bond;

alkynyl is a linear or branched radical having two to about twenty carbon atoms and containing at least one carbon carbon triple bond;

heteroaryl is a fully unsaturated radical having a carbocyclic ring system consisting of one ring or two fused rings, said ring selected from five-membered rings containing one, two or three hetero atoms as ring members selected from nitrogen, oxygen, and sulfur atoms.

4. The method of claim 3 wherein A is selected from CO and $SO_2$; wherein X is selected from oxygen atom, methylene and

with select $R_{10}$ selected from hydrido and methyl; wherein each of $R_1$ and $R_9$ is independently selected from hydrido, lower alkyl, alkoxyacyl, alkoxycarbonyl, benzyloxycarbonyl, haloalkyl and benzyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, phenethyl, cyclohexylmethyl, pyrrolidinyl, piperidinyl, pyrrolidinylmethyl, piperidinylmethyl, pyrazolemethyl, pyrozoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein each of $R_4$ and $R_6$ is independently selected from hydrido and methyl; wherein $R_5$ is selected from hydrido, alkyl, heteroarylalkyl and heteroarylcycloalkyl; wherein $R_7$ is cyclohexylmethyl; wherein $R_8$ is selected from

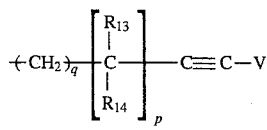

wherein V is selected from hydrido, alkyl and trifluoromethyl; wherein each of $R_{13}$ and $R_{14}$ is a radical independently selected from hydrido, alkyl and alkynyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof;

with the proviso that for any of the foregoing $R^1$ through $R^{14}$ substituents containing a radical selected from alkyl, cycloalkyl, alkenyl, alkynyl, aryl and heterocyclic, the following shall apply:

alkyl is a linear or branched radical having one to about twenty carbon atoms:

alkynyl is a linear or branched radical having two to about twenty carbon atoms and containing at least one carbon carbon triple bond; and heteroaryl is a fully unsaturated radical having a carbocyclic ring system consisting of one ring or two fused rings, said ring selected from five-membered rings containing one, two or three hetero atoms as ring members selected from nitrogen, oxygen, and sulfur atoms.

5. The method of claim 4 wherein A is selected from CO and $SO_2$; wherein X is selected from oxygen atom and methylene; wherein each of $R_1$ and $R_9$ is independently selected from hydrido, methyl, ethyl, n-propyl, isopropyl, benzyl, β,β,β-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, pyrrolidinyl, piperidinyl, pyrrolidinylmethyl, piperidinylmethyl, pyrazolemethyl, pyrozoleethyl, pyridylmethyl, pyridylethyl, thiazolemethyl, thiazoleethyl, imidazolemethyl, imidazoleethyl, thienylmethyl, thienylethyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_5$ is selected from hydrido, alkyl, pyrazolealkyl, pyridylalkyl, thiazolylalkyl, imidazolealkyl, thienylalkyl, thiazolylcycloalkyl, imidazolecycloalkyl, thienylcycloalkyl, furanylalkyl, oxazolylalkyl, isoxazolylalkyl, pyrimidinylalkyl, pyridazinylalkyl and pyrazinylalkyl; wherein $R_7$ is cyclohexylmethyl; wherein $R_8$ is selected from

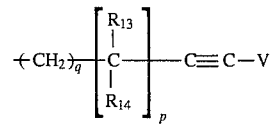

wherein V is selected from hydrido, alkyl and trifluoromethyl; wherein each of $R_{13}$ and $R_{14}$ is a radical independently selected from hydrido, methyl, ethyl, propyl and ethynyl; wherein each of $R_4$ and $R_6$ is independently selected from hydrido and methyl; wherein each of $R_{11}$ and $R_{12}$ is independently selected from hydrido, alkyl, dialkylamino and phenyl; wherein m is zero; wherein n is a number selected from zero through five; wherein p is a number selected from zero through five; and wherein q is a number selected from zero through five; or a pharmaceutically-acceptable salt thereof;

with the proviso that for any of the foregoing $R^1$ through $R^{14}$ substituents containing alkyl, said alkyl is a linear or branched radical having one to about ten carbon atoms.

6. The method of claim 5 wherein A is selected from CO and $SO_2$; wherein X is selected from oxygen atom and methylene; wherein each of $R_1$ and $R_9$ is a group independently selected from hydrido, methyl, ethyl, n-propyl, isopropyl, benzyl, β,β,β-trifluoroethyl, t-butyloxycarbonyl and methoxymethylcarbonyl, and wherein the nitrogen atom to which $R_1$ and $R_9$ are attached may be combined with oxygen to form an N-oxide; wherein $R_2$ is selected from hydrido, methyl, ethyl and isopropyl; wherein $R_3$ is selected from benzyl, cyclohexylmethyl, phenethyl, imidazolemethyl, pyridylmethyl and 2-pyridylethyl; wherein $R_5$ is selected from hydrido, methyl, ethyl, n-propyl, isopropyl, n-butyl, sec-butyl, iso-butyl, tert-butyl, n-pentyl, isopentyl, neopentyl, n-hexyl, pyrazolemethyl, pyrazoleethyl, pyridylmethyl, pyridylethyl, thiazolemethyl, thiazoleethyl, imidazolemethyl, imidazoleethyl, thienylmethyl, thienylethyl, thiazolylcyclopropyl, imidazolecyclopropyl, thienylcyclopropyl, furanylmethyl, furanylethyl, oxazolemethyl, oxazoleethyl, isoxazolemethyl, isoxazoleethyl, pyridazinemethyl, pyridazineethyl, pyrazinemethyl and pyrazineethyl; wherein $R_7$ is cyclohexylmethyl; wherein $R_8$ is selected from

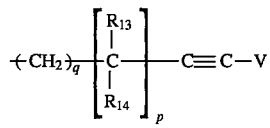

wherein V is selected from hydrido, alkyl and trifluoromethyl; wherein each of $R_{13}$ and $R_{14}$ is a radical independently selected from hydrido, methyl and ethynyl; wherein each of $R_4$ and $R_6$ is independently selected from hydrido and methyl; wherein each of $R_{11}$ and $R_{12}$ is independently selected from hydrido, alkyl and phenyl; wherein m is zero; wherein n is a number selected from zero through three; wherein p is a number selected from one through three; and wherein q is zero or one; or a pharmaceutically-acceptable salt thereof;

with the proviso that for any of the foregoing $R^1$ through $R^{14}$ substituents containing alkyl, said alkyl is a linear or branched radical having one to about ten carbon atoms.

7. The method of claim 6 wherein said compound is selected from compounds, their tautomers, and the pharmaceutically-acceptable esters and salts thereof, of the group consisting of

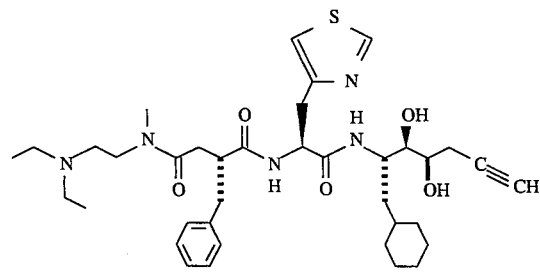

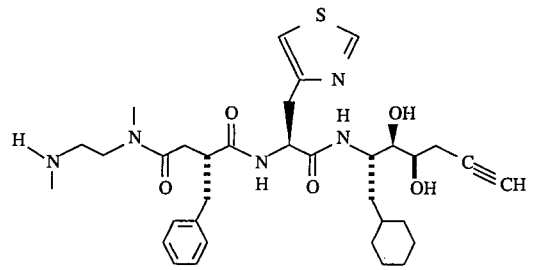

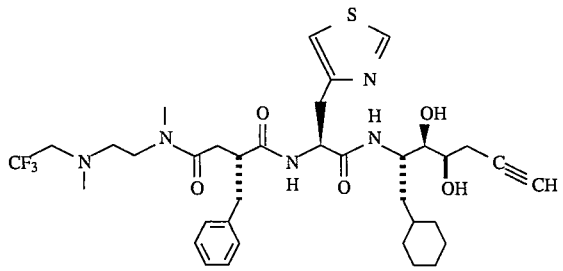

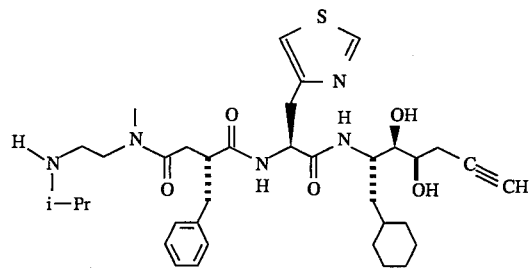

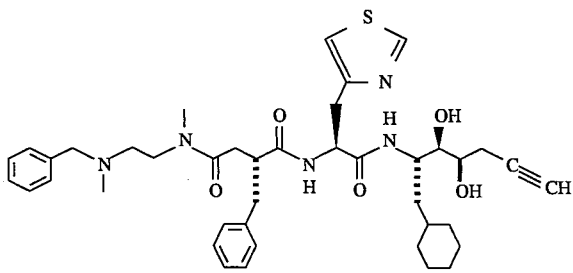

and

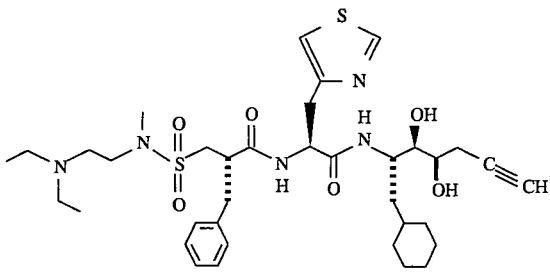

8. The method of claim 6 wherein said compound is

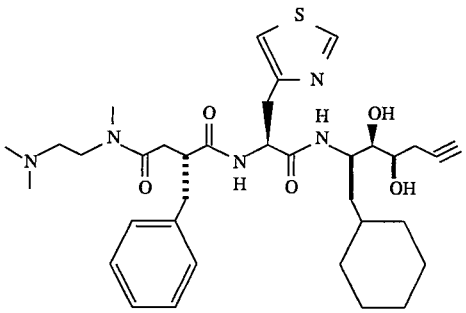

or a pharmaceutically-acceptable salt thereof.

9. The method of claim 6 wherein said compound is

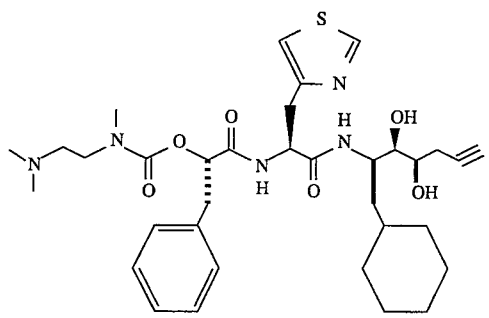

or a pharmaceutically-acceptable salt thereof.

10. The method of claim 6 wherein said compound is
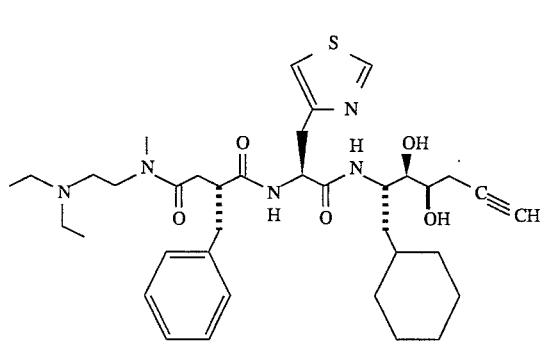
or a pharmaceutically-acceptable salt thereof.
11. The method of claim 6 wherein said compound is
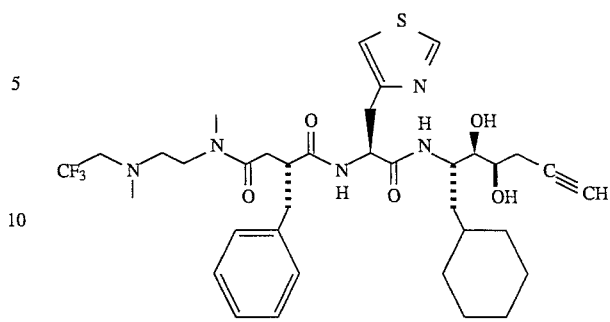
or a pharmaceutically-acceptable salt thereof.
* * * * *